US008731651B2

(12) United States Patent
Ben-David et al.

(10) Patent No.: US 8,731,651 B2
(45) Date of Patent: May 20, 2014

(54) REGULATING UTERINE MUSCULAR ACTIVITY

(75) Inventors: Gal Ben-David, Adi (IL); Tamir Ben-David, Tel Aviv (IL); Ilan Calderon, Bet Lechem Haglilit (IL)

(73) Assignee: OB Tools Ltd., Migdal HaEmek (IL)

( * ) Notice: Subject to any disclaimer, the term of this patent is extended or adjusted under 35 U.S.C. 154(b) by 0 days.

(21) Appl. No.: 13/540,791

(22) Filed: Jul. 3, 2012

(65) Prior Publication Data

US 2014/0012190 A1    Jan. 9, 2014

(51) Int. Cl.
*A61B 5/04*    (2006.01)

(52) U.S. Cl.
USPC ........................................................ 600/546

(58) Field of Classification Search
CPC .............................. A61B 5/4346; A61B 5/0444
USPC ............................................ 604/66; 600/546
See application file for complete search history.

(56) References Cited

U.S. PATENT DOCUMENTS

| | | | | |
|---|---|---|---|---|
| 5,520,637 A | * | 5/1996 | Pager et al. ...................... | 604/66 |
| 5,546,953 A | * | 8/1996 | Garfield ......................... | 600/546 |
| 5,776,073 A | * | 7/1998 | Garfield et al. ............... | 600/546 |
| 6,173,198 B1 | * | 1/2001 | Schulze et al. ................ | 600/382 |
| 6,725,094 B2 | * | 4/2004 | Saberski ......................... | 607/46 |
| 6,816,744 B2 | * | 11/2004 | Garfield et al. ............... | 600/546 |
| 7,447,542 B2 | * | 11/2008 | Calderon et al. ............... | 600/546 |
| 7,850,625 B2 | * | 12/2010 | Paltieli et al. ................. | 600/588 |
| 7,925,323 B2 | * | 4/2011 | Meyer .......................... | 600/382 |
| 2002/0068960 A1 | * | 6/2002 | Saberski et al. ............... | 607/46 |
| 2002/0193670 A1 | * | 12/2002 | Garfield et al. ............... | 600/304 |
| 2005/0010127 A1 | * | 1/2005 | Calderon et al. .............. | 600/546 |
| 2007/0179362 A1 | * | 8/2007 | Chou ............................ | 600/301 |
| 2008/0167553 A1 | * | 7/2008 | Paltieli et al. ................. | 600/437 |
| 2010/0022865 A1 | * | 1/2010 | Meyer .......................... | 600/393 |
| 2010/0286735 A1 | * | 11/2010 | Garfield et al. .................... | 607/3 |
| 2012/0150010 A1 | * | 6/2012 | Hayes-Gill et al. ........... | 600/382 |
| 2012/0238894 A1 | * | 9/2012 | Principe et al. ............... | 600/546 |

* cited by examiner

*Primary Examiner* — Aarti B Berdichevsky
(74) *Attorney, Agent, or Firm* — Dekel Patent Ltd.; David Klein

(57) ABSTRACT

A method and system for regulating uterine muscular activity including measuring uterine contraction with an electrical uterine monitor (EUM), and using sensed measurements of the uterine contraction to regulate uterine muscular activity by comparing the sensed measurements to a desired level, wherein the difference between sensed and desired level is used to calculate the level of either manual or automatic application of drugs or electrical signals.

16 Claims, 4 Drawing Sheets

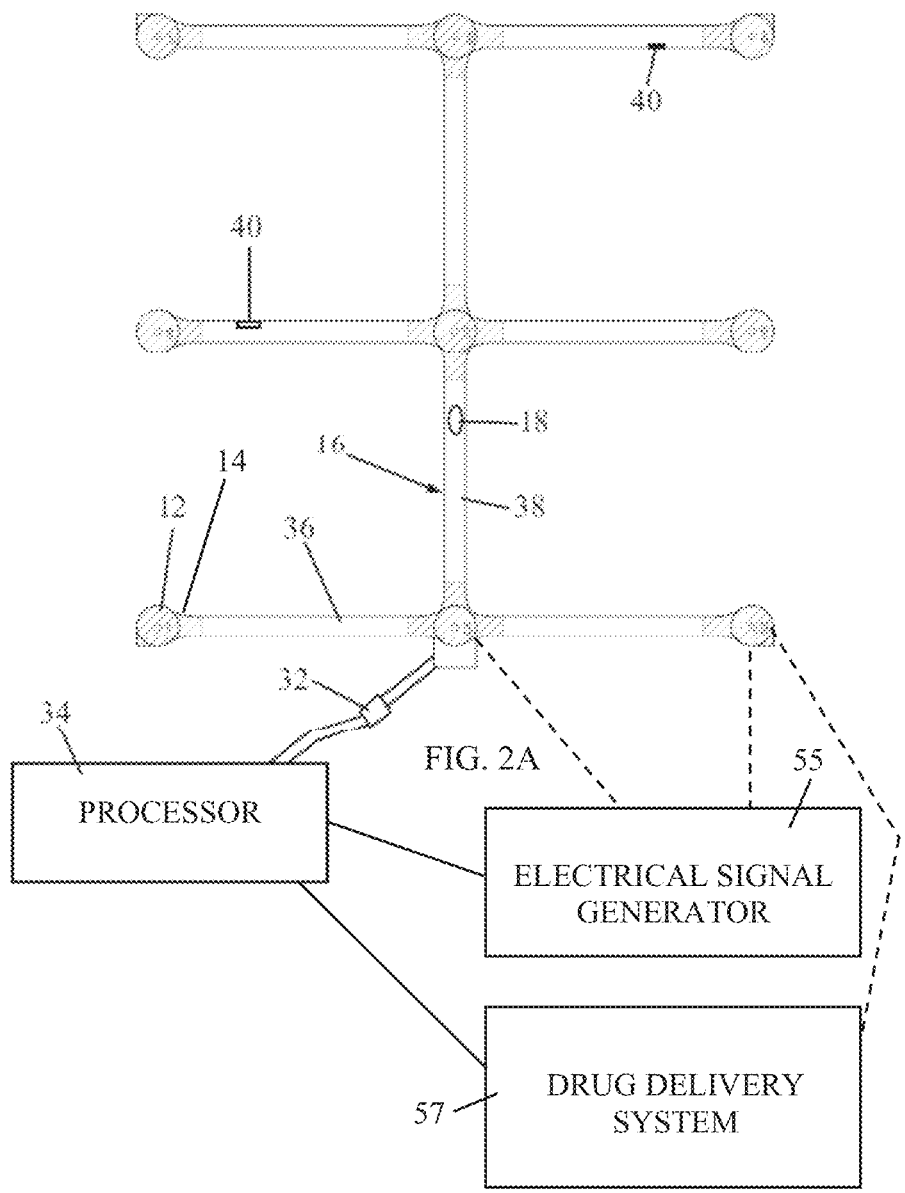

REGULATING UTERINE MUSCULAR ACTIVITY

FIELD OF THE INVENTION

The present invention relates generally to methods and systems for regulating uterine muscular activity based on EMG (electromyographic) measurement.

BACKGROUND OF THE INVENTION

Active management of labor is known (e.g., "Active Management of Labor", Jason A. Pates, MD, Andrew J. Satin, MD, Department of Obstetrics and Gynecology, Uniformed Services University of the Health Sciences, 4301 Jones Bridge Road, Bethesda, Md. 20814, USA, Obstet Gynecol Clin N Am 32 (2005) 221-230). Management of pre-term labor activity has also been discussed (see, for example, "Management of preterm labor", ACOG Practice Bulletin No. 43. American College of Obstetricians and Gynecologists. Obstet Gynecol 2003; 101:1039-47; and King J F, Flenady V, Papatsonis D, Dekker G, Carbonne B, "Calcium channel blockers for inhibiting preterm labour", *Cochrane Database of Systematic Reviews* 2003, Issue 1. Art. No.: CD002255. DOI: 10.1002/14651858.CD002255).

However, despite knowing how to increase or reduce uterine activity, heretofore no one has described or hinted at increasing or reducing uterine activity (such as labor or pre-term labor) by sensing uterine activity with controlled loop activity management, as will be described below in the description of embodiments of the invention. This has significant advantages over the prior art. For example, use of tocolytic drugs is expensive and may cause side effects. Use of electrical signals to inhibit or to intensify contraction may also have side effects. Use of contraction augmentation hormones may cause fetal stress. By sensing uterine activity with controlled loop activity management, the cost and possible side effects are reduced or eliminated.

SUMMARY OF THE INVENTION

The present invention is directed, among other things, to methods and systems for regulating uterine muscular activity based on EMG measurement, as is described more in detail hereinbelow. The muscular activity may be controlled by using drugs and/or electrical stimulation. The system can be implemented as a closed loop control system, wherein control decisions may be automatic or human based (physician decision).

There is thus provided in accordance with a non-limiting embodiment of the present invention a method and system for regulating uterine muscular activity including measuring uterine contraction with an electrical uterine monitor (EUM), and using sensed measurements of the uterine contraction to regulate uterine muscular activity by comparing the sensed measurements to a desired level, wherein the difference between sensed and desired level is used to calculate the level of either manual or automatic application of a drug or electrical signal.

The EUM and processor may operate in a control loop with an electrical signal generator or drug delivery system for automatic application of the electrical signal or drug.

BRIEF DESCRIPTION OF THE DRAWINGS

The present invention will be understood and appreciated more fully from the following detailed description taken in conjunction with the appended drawings in which:

FIG. 2A is a simplified illustration of the system, in accordance with a non-limiting embodiment of the present invention, including an electrical uterine monitor (EUM) that operates with an electrical signal generator and/or drug delivery system;

DETAILED DESCRIPTION OF EMBODIMENTS

Figure 1:
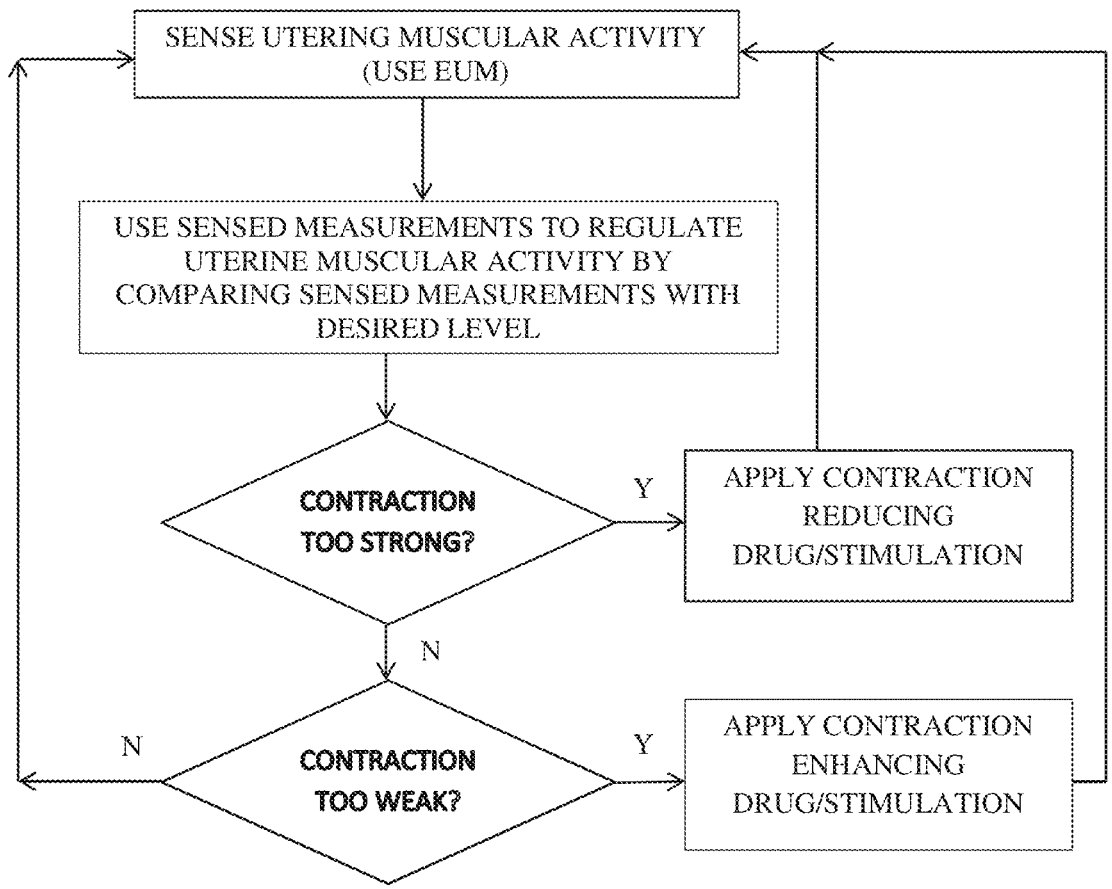
FIG. 1 is a simplified flow chart of a system/method for regulating uterine muscular activity (uterine contraction) based on EMG measurement, in accordance with a non-limiting embodiment of the present invention.

Reference is now made to FIG. 1, which is a flow chart of a system/method for regulating uterine muscular activity (uterine contraction) based on EMG measurement, in accordance with a non-limiting embodiment of the present invention. In one non-limiting embodiment of the invention, measuring uterine contraction is done with an electrical uterine monitor (EUM), examples of which are described below with reference to FIGS. 2A-2B and 3. The sensed measurements are used to regulate uterine muscular activity by continuously comparing the sensed measurements to a desired level. If the measured contraction amplitude is stronger than the desired level, a contraction reduction drug or pulse is applied. If the measured contraction amplitude is too weak, a contraction enhancer is applied. The difference between the desired and actual contraction levels may be defined as an error signal. The level of control may be proportional to the error signal or may be a proportional/integral/differential (PID controller) of the error signal. Other control methods such as a bang-bang controller (on-off controller), also known as a hysteresis controller, may be employed.

Uterine activity may be increased or decreased. In accordance with a non-limiting embodiment of the invention, uterine activity may be increased using electrical stimulation (see Obstet Gynecol. 1989 February; 73(2):286-90, "Transcutaneous Electrical Nerve Stimulation At Acupuncture Points In The Induction Of Uterine Contractions", Dunn P A, Rogers D, Halford K. Physiotherapy Department, Moorabbin Hospital, Melbourne, Australia; and Biol Reprod. 2008 October; 79(4):633-7. Epub 2008 Jun. 11, "Stimulation of fetal hypothalamus induces uterine contractions in pregnant rats at term", Endoh H, Fujioka T, Endo H, Inazuka Y, Furukawa S, Nakamura S. Department of Neuroscience and of Reproductive, Yamaguchi University Graduate School of Medicine, Ube, Yamaguchi 755-8505, Japan); and/or oxytocin activity (see Lee H J, Macbeth A H, Pagani J H, Young W S (June 2009). "Oxytocin: the Great Facilitator of Life". Progress in Neurobiology 88 (2): 127-51. doi:10.1016/j.pneurobio.2009.04.001). For example, intravenous administration of dilute oxytocin is commonly used to increase uterine activity.

In accordance with a non-limiting embodiment of the invention, uterine activity may be reduced by using tocolytics (see Br J Obstet Gynaecol. 1987 November; 94(11):1040-4, "Inhibition of uterine contractions of premature labour with an oxytocin analogue. Results from a pilot study", Akerlund M, Stromberg P, Hauksson A, Andersen L F, Lyndrup J, Trojnar J, Melin P, Department of Obstetrics and Gynecology, University Hospital, Lund, Sweden); and/or interference electrical signals (see Am J Obstet Gynecol. 2005 December; 193(6):1986-93, "Electrical inhibition of preterm birth: inhibition of uterine contractility in the rabbit and pup births in the rat", Karsdon J, Garfield R E, Shi S Q, Maner W, Saade G. Neonatology Department, New York Downtown Hospital, New York, N.Y. 10038-2649, USA. Jeffrey.Karsdon@downtownhospital.org.). Examples of tocolytics are, without limitation, intravenous administration of Atosiban, xanthines, theophylline and aminophylline.

In one embodiment of the invention, during active labor the clinician (e.g., midwife or physician) regulates uterine activity to a level that will cause progress in cervix dilatation and fetal head station on one hand, but will not cause stress on the fetus on the other hand. In this embodiment, the system uses closed loop control using the EUM as the uterine activity sensor and a dose of electrical stimulation/oxytocin as the control method. Note that there is only activity increase control but no activity reduction control.

Automatic application of drugs may be done by electronically operated drug dispensers (transdermal patches, invasive (needle) dispensers, intravenous dispensers and many others), which are in communication with the EUM sensor.

In another embodiment of the invention, if pre-term uterine activity appears, the system reduces uterine activity to a level that will not cause pre-term labor. By sensing uterine activity with controlled loop activity management, the system uses the minimum amount of drugs/signals as needed to reduce uterine activity to the desired level. Note that there is only activity decrease control but no activity increase control.

In another embodiment of the invention, the system is used to treat non-pregnant women who experience spontaneous contractions.

Uterine contractions can occur in non-pregnant women during menstruation, which cause significant pain (see Aguilar, H. N.; Xiao, S.; Knoll, A. H.; Yuan, X. (2010). "Physiological pathways and molecular mechanisms regulating uterine contractility". Human Reproduction Update 16 (6): 725-744. doi:10.1093/humupd/dmq016. JSTOR 1306737. PMID 20551073). The uterine activity sensor detects the level of uterine contraction and the effect of a tocolytics drug on the contraction. Such uterine contraction measurement can help minimize or eliminate drug/signal usage, while reducing uterine activity to the desired level. Note that there is only activity decrease control but no activity increase control.

In another set up, such a sensor can be used for the diagnosis of pain (not just control of the pain), resulting from uterine contractions, specifically during menstruation. The sensed uterine activity is compared to known (previously measured or otherwise stored) uterine contractions due to menstruation, and a diagnosis can be made if the sensed uterine activity is indicative of menstrual uterine contraction.

In another embodiment of the invention, the system is used to treat non-pregnant women who experience induced contractions.

Uterine contractions can occur in non-pregnant women when the uterus is stimulated by a medical operation. One example is during IVF embryo transfer (see "Uterine contractions at the time of embryo transfer alter pregnancy rates after in-vitro fertilization", R Fanchin, C Righini, F Olivennes, S Taylor, D de Ziegler and R Frydman, Department of Obstetrics and Gynaecology and Reproductive Endocrinology, Hôpital Antoine Béclère, Clamart, France, Oxford Journals, Human Reproduction, Volume 13, Issue 7, Pp. 1968-1974). The objective is to use as little drugs/electrical inhibitor signals as needed to reduce uterine activity to the desired level (or even prevent contraction completely). This may be a single stage (phase) or a two-stage (or multi-stage) protocol.

In the two-stage protocol, during the first stage, a test is made by applying the stimulation (inserting a catheter) without actual medical effect. The uterine response is recorded using the sensor (EUM). During the second phase, during actual medical treatment, the control tocolytic is applied, based on the first stage and/or real time analysis of uterine activity. In another setup uterine activities are measured and regulated after IVF embryo transfer for a period of up to few weeks to detect unwanted uterine contraction.

Figure 2B:
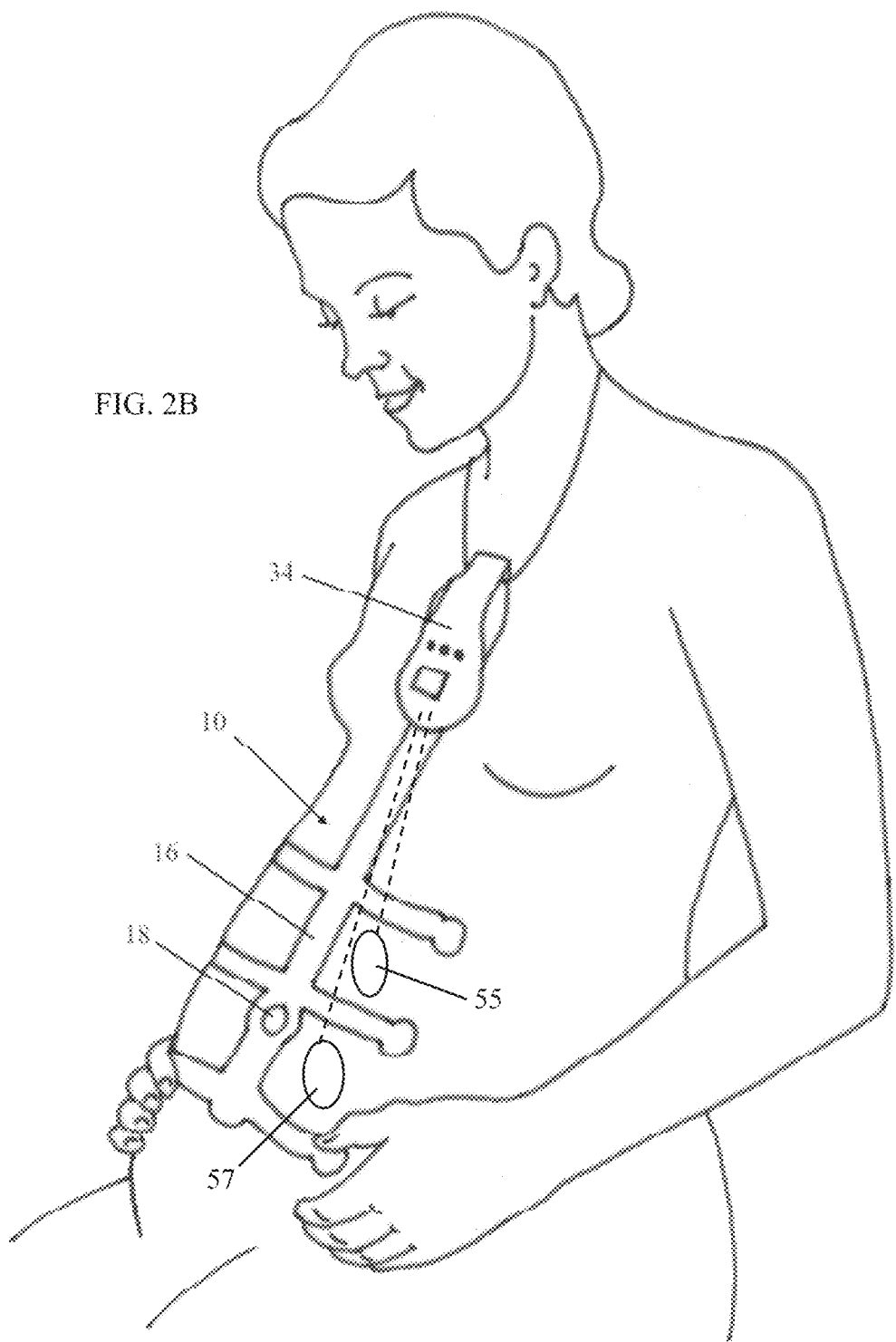
FIG. 2B is a simplified illustration of the EUM as part of a uterine monitor (home or hospital/clinic system), cooperating with an electrical signal generator and/or drug delivery system, in accordance with a non-limiting embodiment of the present invention.

Reference is now made to FIGS. 2A-2B, which illustrate one example of an EUM 10, which is described in U.S. Pat. No. 7,447,542. Briefly, U.S. Pat. No. 7,447,542 describes an improved system for three-dimensional monitoring (e.g., measuring, imaging and displaying) of myographic uterine activity. The system includes an electromyogram (EMG) system that senses electromyographic activity generated in a muscle, one or more position sensors, and a processor in communication with the EMG system and the position sensors. The processor processes data of the EMG system and the three-dimensional position information from the position sensors to provide an output of electromyographic activity in the three dimensional space, providing contraction intensity data as a function of time. As opposed to prior art intra-uterine pressure catheters, the EUM measurement is non-invasive. Another known technology, the toco-dynamometer, does not provide contraction intensity information.

EUM 10 (or EUM electrode 10) includes one or more uterine electrical activity sensors 12 mounted on a substrate 14, which is placed on the abdominal wall of the pregnant or non-pregnant woman. Substrate 14 may be in the form of a "tree" 16, with the sensors 12 mounted on a portion of "branches" 36 that extend from a "trunk" 38. One or more fiduciary marks 18 are provided to enable repeatable positioning of EUM 10, i.e., positioning EUM 10 at the same place on the abdomen at each use. Uterine electrical activity sensors 12 may include electromyogram (EMG) electrodes, such as but not limited to, nine EMG surface recording Ag/AgCl electrodes and an optional reference electrode.

Substrate 14 may be formed with non-symmetrical identification elements 40, such as cutouts or other markings (e.g., particular geometric shapes, such as triangles or hexagons, placed at pre-determined positions), in order to prevent incorrect mounting of the device on the abdomen.

The three-dimensional position and orientation of each uterine activity sensor 12 is known as described above using an off the shelf position sensor or using the known structure of the electrode. Processor 34 processes electrical signals of the uterine activity sensors 12 and the three-dimensional position and orientation to provide an output that comprises electromyographic activity data as a mathematical function of the three-dimensional position and orientation of the uterine activity sensor 12. This provides contraction intensity data as a function of time, by using, for example, the integral of electromyographic activity over all the uterus volume.

EUM electrode 10 is generally intended for single use only, staying functional for at least 18 hours (relatively long labor time), for example. However, the invention is not limited to such a device and the invention can be used for multiple uses as well.

EUM electrode 10 is able to identify individual sensors 12 and their positions. For example, the sensors 12 may be marked in numbers left to right, top to bottom, and/or may be color-coded and/or may be each uniquely shaped, for easy visual identification. Additionally or alternatively, each sensor 12 may be assigned a unique position code that processor 34 identifies, so that the position of each sensor 12 is known.

In FIG. 2B, EUM 10 is provided as part of a uterine monitor (home or hospital/clinic) system. EUM 10 is attached to the woman in the confines of her home. EUM 10 senses or monitors data, performs local control of contractions, and/or communicates the data to a remote site (e.g., a website) via processor 34, also referred to as EUM unit 34 (which may be worn around the neck or mounted on another part of the body) to perform a remote regulation of the contractions.

In both FIGS. 2A and 2B, the sensors 12 and processor 34 of EUM 10 cooperate with an electrical signal generator 55 (e.g., electrodes, electrical stimulating apparatus, electrical interference signals, and the like) and/or drug delivery system 57 (e.g., intravenous, hypodermic needle, transdermal patch, and others) for administrating electrical stimulation or interference and/or drugs, as described above.

Figure 3:
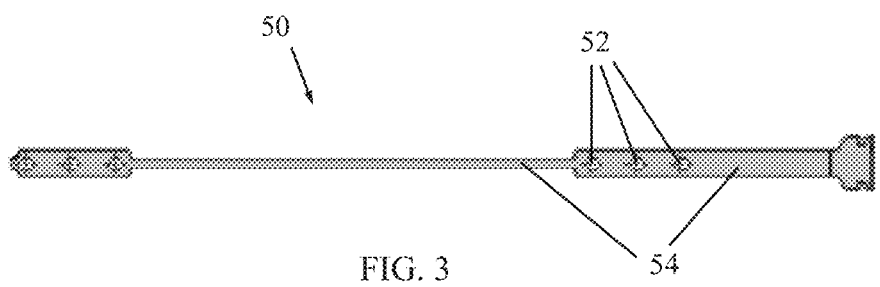
FIG. 3 is a simplified illustration of an EUM, in accordance with a non-limiting embodiment of the present invention.

Reference is now made to FIG. 3. For non-pregnant women, the uterus is small, so instead of the embodiment of FIGS. 2A-2B, an electrode array 50 is used to sense the electrical activity of the uterus. The electrode array 50 includes one or more uterine electrical activity sensors 52 mounted on a substrate 54 (similar to electrical activity sensors 12 and substrate 14 of FIGS. 2A-2B). Substrate 54 may be in the form of a strap which may be wrapped around the torso or other portion of the woman. Since the patient is not pregnant, electrodes may be placed both on the back and the abdomen, for example.

Since during some operations, e.g., IVF embryo transfer, the clinician uses ultrasound modality to navigate the catheter, the electrode array design may have an area with no electrodes to allow access to the ultrasound probe.

It is appreciated that various features of the invention which are, for clarity, described in the contexts of separate embodiments, may also be provided in combination in a single embodiment. Conversely, various features of the invention which are, for brevity, described in the context of a single embodiment, may also be provided separately or in any suitable subcombination.

What is claimed is:

1. A method for regulating uterine muscular activity comprising:
   measuring uterine contraction with an electrical uterine monitor (EUM), said EUM comprising uterine electrical activity sensors that output to a processor, wherein the measuring comprises processing electrical signals of the uterine electrical activity sensors to determine a measured amount of uterine contraction; and
   using sensed measurements of the uterine contraction to regulate uterine muscular activity by comparing the sensed measurements to a desired level, said desired level being defined and stored before said measuring, wherein the difference between sensed and desired level is used to calculate the level of either manual or automatic application of a drug or electrical signal, comprising defining the difference between the sensed and the desired levels as an error signal and regulating the uterine muscular activity with a level of control proportional to the error signal.

2. The method according to claim 1, comprising regulating the uterine muscular activity to a level that causes progress in cervix dilatation and fetal head station, but does not cause stress on a fetus.

3. The method according to claim 1, comprising regulating the uterine muscular activity to a level that does not cause pre-term labor.

4. The method according to claim 1, wherein said uterine muscular activity is increased.

5. The method according to claim 4, wherein said uterine muscular activity is increased using electrical stimulation.

6. The method according to claim 4, wherein said uterine muscular activity is increased by administering oxytocin.

7. The method according to claim 1, wherein said uterine muscular activity is decreased.

8. The method according to claim 7, wherein said uterine muscular activity is decreased by administering a tocolytic.

9. The method according to claim 7, wherein said uterine muscular activity is decreased by using interference electrical signals.

10. The method according to claim 1, comprising regulating the uterine muscular activity to treat a non-pregnant woman who experiences contractions.

11. The method according to claim 10, wherein said non-pregnant woman experiences contractions during menstruation.

12. The method according to claim 10, wherein said non-pregnant woman experiences contractions during an IVF procedure.

13. A system for regulating uterine muscular activity comprising:
   an electrical uterine monitor (EUM) for measuring uterine contraction, said EUM comprising uterine electrical activity sensors in operative communication with a processor; and
   wherein said processor is operative to use sensed measurements of the uterine contraction to regulate uterine muscular activity by comparing the sensed measurements to a desired level, wherein the difference between sensed and desired level is used to calculate the level of either manual or automatic application of a drug or electrical signal, and wherein said processor is operative to define the difference between the sensed and the desired levels as an error signal and to regulate the uterine muscular activity with a level of control proportional to the error signal.

14. The system according to claim 13, wherein said EUM and said processor operate in a control loop with an electrical signal generator or drug delivery system for automatic application of the electrical signal or drug.

15. The system according to claim 13, wherein said uterine muscular activity is increased.

16. The system according to claim 13, wherein said uterine muscular activity is decreased.

* * * * *